United States Patent
Lee et al.

(10) Patent No.: US 12,339,444 B2
(45) Date of Patent: Jun. 24, 2025

(54) NATURAL PHYSIO-OPTICAL USER INTERFACE FOR INTRAOCULAR MICRODISPLAY

(71) Applicant: Verily Life Sciences LLC, Dallas, TX (US)

(72) Inventors: Shungneng Lee, Sunnyvale, CA (US); Supriyo Sinha, Menlo Park, CA (US); Dimitri Azar, Chicago, IL (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

(21) Appl. No.: 18/542,155

(22) Filed: Dec. 15, 2023

(65) Prior Publication Data
US 2024/0126075 A1    Apr. 18, 2024

Related U.S. Application Data

(63) Continuation of application No. 17/609,752, filed as application No. PCT/US2020/024195 on Mar. 23, 2020, now Pat. No. 11,874,462.
(Continued)

(51) Int. Cl.
    *G02B 27/00*    (2006.01)
    *A61F 2/14*     (2006.01)
    *G02B 27/01*    (2006.01)

(52) U.S. Cl.
    CPC ............ *G02B 27/0093* (2013.01); *A61F 2/14* (2013.01); *G02B 27/0101* (2013.01);
    (Continued)

(58) Field of Classification Search
    CPC ................. G06F 3/011; G06T 2207/30204
    See application file for complete search history.

(56) References Cited

U.S. PATENT DOCUMENTS 6,771,294 B1 * 8/2004 Pulli ................. G06F 3/011
                                                    715/764
7,496,174 B2   2/2009 Gertner et al.
(Continued)

FOREIGN PATENT DOCUMENTS

CN    108108022    6/2018
EP    1585462     2/2017
(Continued)

OTHER PUBLICATIONS

International Search Report and Written Opinion for International Application No. PCT/US2020/024195 mailed Jun. 22, 2020, 10 pages.
(Continued)

*Primary Examiner* — Nan-Ying Yang
(74) *Attorney, Agent, or Firm* — Haynes and Boone, LLP

(57) ABSTRACT

An intraocular micro-display (IOMD) system includes an auxiliary head unit. The auxiliary head unit includes a frame for mounting to a head of a user, a scene camera module mounted in or on the frame in a forward-facing orientation, a gaze tracking module disposed in or on the frame and configured to monitor an eye of the user, and an auxiliary controller. The auxiliary controller includes for: acquiring a scene image with the scene camera module, determining a gazing direction of the eye based upon gaze direction data from the gaze tracking module, identifying a sub-portion of the scene image based upon the gazing direction, and wirelessly relaying the sub-portion of the scene image to an IOMD implant within the eye for displaying to a retina of the eye.

19 Claims, 8 Drawing Sheets

Related U.S. Application Data

(60) Provisional application No. 62/846,443, filed on May 10, 2019.

(52) U.S. Cl.
CPC .... *G02B 27/017* (2013.01); *A61F 2250/0002* (2013.01); *G02B 2027/0138* (2013.01); *G02B 2027/0178* (2013.01)

(56) References Cited

U.S. PATENT DOCUMENTS

| | | | |
|---|---|---|---|
| 8,945,197 B1 * | 2/2015 | Friend | A61N 5/06 |
| | | | 607/88 |
| 9,042,028 B2 | 5/2015 | Choi et al. | |
| 9,791,700 B2 | 10/2017 | Schowengerdt | |
| 9,997,585 B2 | 6/2018 | Kasai | |
| 10,025,379 B2 | 7/2018 | Drake et al. | |
| 10,251,780 B2 | 4/2019 | Tai et al. | |
| 10,386,655 B2 | 8/2019 | Lee et al. | |
| 11,874,462 B2 | 1/2024 | Lee et al. | |
| 2011/0169998 A1 | 7/2011 | Canetti | |
| 2012/0127062 A1 | 5/2012 | Bar-Zeev et al. | |
| 2014/0300632 A1 * | 10/2014 | Laor | G06T 19/006 |
| | | | 345/633 |
| 2015/0003819 A1 | 1/2015 | Ackerman et al. | |
| 2015/0109191 A1 | 4/2015 | Johnson | |
| 2015/0205457 A1 * | 7/2015 | Woo | G06F 3/0482 |
| | | | 715/767 |
| 2016/0025971 A1 | 1/2016 | Crow et al. | |
| 2016/0029883 A1 | 2/2016 | Cox | |
| 2016/0050345 A1 | 2/2016 | Longbotham et al. | |
| 2016/0313798 A1 | 10/2016 | Connor | |
| 2017/0330042 A1 | 11/2017 | Vaziri | |
| 2017/0336641 A1 | 11/2017 | von und zu Liechtenstein | |
| 2018/0120936 A1 | 5/2018 | Keller et al. | |
| 2018/0144196 A1 * | 5/2018 | Vaziri | G06V 20/52 |
| 2018/0249072 A1 * | 8/2018 | Li | G06V 40/103 |
| 2018/0256316 A1 | 9/2018 | Deering et al. | |
| 2019/0025688 A1 | 1/2019 | Maynard | |
| 2019/0109536 A1 | 4/2019 | Lee | |
| 2020/0197223 A1 * | 6/2020 | Yu | A61F 2/14 |

FOREIGN PATENT DOCUMENTS

| | | |
|---|---|---|
| EP | 1996968 | 3/2017 |
| GB | 2482076 | 1/2012 |
| WO | 2006015315 | 2/2006 |
| WO | 2008153592 | 12/2008 |
| WO | 2018058155 | 3/2018 |
| WO | 2018222357 | 12/2018 |
| WO | 2019055477 | 3/2019 |
| WO | WO-2019055477 A2 * | 3/2019 ............... A61F 2/14 |

OTHER PUBLICATIONS

"Argus II: the life-changing retinitis pigmentosa treatment," SecondSight, retrieved from the Internet <https://www.secondsigh.com/discover-argus/>, May 20, 2019, 8 pages.

Shim, BS, Sarah Y., et al., "Feasability of Intraocular Projection for Treatment of Intractable Corneal Opacity," Corenea, vol. 38, No. 4, Apr. 2019, pp. 523-527.

International Search Report and Written Opinion for International Application No. PCT/US2020/024201 mailed Jun. 29, 2020, 11 pages.

Notice of the Reason for Refusal for Japanese Application No. 2021-566983 mailed Jan. 4, 2023, 9 pages.

Extended European Search Report for European Application No. 20806439.4 mailed Dec. 9, 2023, 16 pages.

* cited by examiner

NATURAL PHYSIO-OPTICAL USER INTERFACE FOR INTRAOCULAR MICRODISPLAY

CROSS-REFERENCE TO RELATED APPLICATIONS

This patent application is a continuation application of co-pending U.S. patent application Ser. No. 17/609,752 filed Nov. 8, 2021, which is a U.S. National Phase Application under 35 U.S.C. § 371 of International Application PCT/US2020/024195 filed Mar. 23, 2020, which claims the benefit of U.S. Provisional Application No. 62/846,443, filed May 10, 2019, which are hereby incorporated by reference in their entirety.

TECHNICAL FIELD

This disclosure relates generally to ophthalmic devices, and in particular, relates to intraocular micro-displays.

BACKGROUND INFORMATION

Disease or injury to the cornea can lead to opacification or significant optical damage to the cornea, such that the individual is effectively rendered blind. The blindness may occur despite the patient having a fully functioning retina. For these patients with an intact retina but otherwise blind due to vascularization or damage to the cornea, implantation of an intraocular micro-display in the excised lens of the eye (e.g., capsular sack region) can restore image reproduction onto their fully functioning retina, thereby returning vision to the patient.

A proposed solution for an electronic intraocular micro-display involves the use of a transcutaneous tether that couples a transmitter positioned behind the ear to the intraocular micro-display. This tether provides power and data communication to the intraocular micro-display. The transcutaneous nature and complex surgery required for this proposed solution, likely makes this solution prone to physiological compatibility issues and inflammation. Since the tether protrudes outside of the eye and back into subcutaneous flesh on the side of the face, the tether also presents an infection risk.

To avoid the use of a transcutaneous tether, the intraocular micro-display and related circuitry must have a sufficiently compact form factor to fit entirely within the eye in the region of the capsular sack. As such, the electronics and user interface of such a small intraocular display present significant challenges. For example, when a user's natural crystalline lens is replaced with an intraocular micro-display, the user loses their natural ability to pan or tilt their forward vision (e.g., look around a scene) simply by moving their eyes. Furthermore, their ability to adjust their focal distance (e.g., accommodate) on different items at different offset distances is also lost. The loss of their natural mechanisms associated with healthy vision can substantially impact the user experience with an intraocular micro-display.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
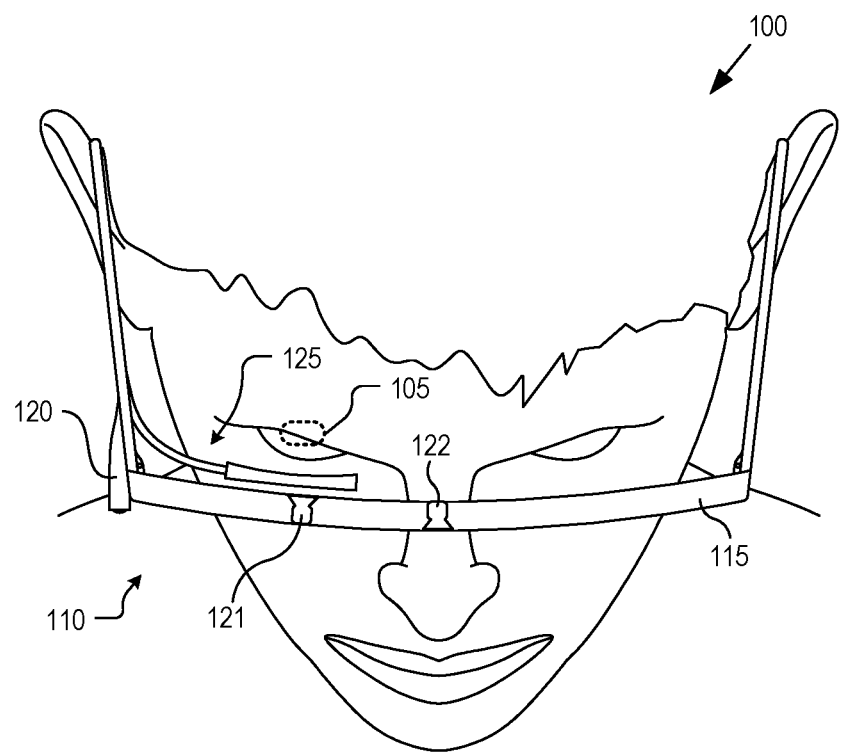
FIGS. 1A and 1B are plan and side view illustrations of an intraocular micro-display (IOMD) system including an IOMD implant and an auxiliary head unit, in accordance with an embodiment of the disclosure.

Embodiments of a system, apparatus, and method of operation for an intraocular micro-display (IOMD) system that provides a natural physio-optical user interface are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of the IOMD system disclosed herein are suitable for patients with intact retinas, yet are blind due to vascularization, occlusion, opacity, or otherwise damage of the cornea. The disclosed IOMD system seeks to restore sight to these patients by implanting an electronic micro-display (referred to as an intraocular micro-display or IOMD) into the eye, such as in the capsular sack region of the eye previously occupied by an excised lens. The IOMD is included within an IOMD implant to project regenerated images onto the patient's fully functioning retina.

Natural healthy vision comes with a real-time natural physio-optical user interface that provides the individual with a holistic user experience. For example, when the individual pans or tilts their eyes in a certain direction, the scene image delivered to their retina automatically changes as their gaze directions scans across the scene in front of them. Thus, immediate real-time feedback is provided to the user that synchronizes with, and otherwise confirms, their muscle action to pivot their eyes. Additionally, when a user directs their gaze upon a specific item, their eyes automatically accommodate (adjust their focal distance) to bring the item in the center of their foveal vision into focus. Finally, when an individual with healthy vision blinks or otherwise closes their eyelids, their vision of the external world is interrupted. All of these real-time physio-optical feedback mechanisms provide an individual with healthy vision a helpful physio-optical interface and holistic user experience that can be lost when their crystalline lens is replaced with an IOMD.

Accordingly, embodiments described herein attempt to simulate one or more of the natural physio-optical interfaces described above to provide the user with a natural, holistic physio-optical user experience. In one embodiment, a gaze tracking module (e.g., eye-ward facing camera) is provided to monitor movements of the user's eye to generate gaze direction data that is indicative of the user's gazing direction and use this data to select a sub-portion of a scene image and present this sub-portion to the user's retina. In other words, a forward-facing scene camera module may acquire a high resolution scene image, from which a sub-portion is selected and delivered to the retina via the IOMD implant. Selection of the sub-portion from an otherwise larger scene image simulates the natural physio-optical interface of scanning a scene by panning or tilting just one's eyes. In addition, the eye-ward facing camera can look for saccades and "jitter" the image accordingly to prevent saturation of the stimulation of retinal cells.

In one embodiment, the physio-optical interface of accommodation is simulated with the use of a near-vision fiducial. The near-vision fiducial may be a visual marker that can be attached to items that are typically the focus of visual attention when brought sufficiently close to the center of our field of view (FOV). For example, when hands are brought into our FOV, they are often at the correct focal distance for what we are doing. In other words, an individual is using their hands to do something, such as holding a book while reading, tying their shoes, cooking, or otherwise. Accordingly, by wearing, or otherwise adhering a near-vision fiducial, on or near the wrist, hand, finger, or thumb, the near-vision fiducial provides a visual marker which may be identified and autofocused upon with high fidelity.

In one embodiment, the gaze tracking module (or other eye-ward facing camera) may be used to monitor the eye for eyelid closure (blinks or longer closures). The identification of these closures may be used to then temporarily cease projecting the regenerated image onto the retina. This physio-optical interface feature simulates blinking or otherwise closing the eyes. It should be appreciated that one, some, or all of the above physio-optical interface features may be implemented individually or collectively in a single embodiment.

Figure 1B:
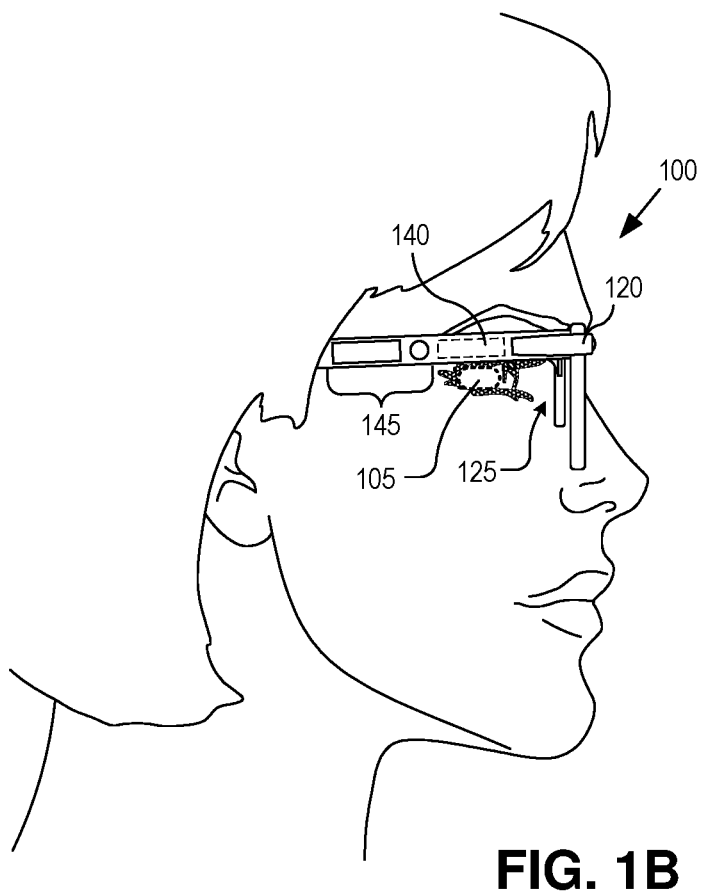
Figure 1C:
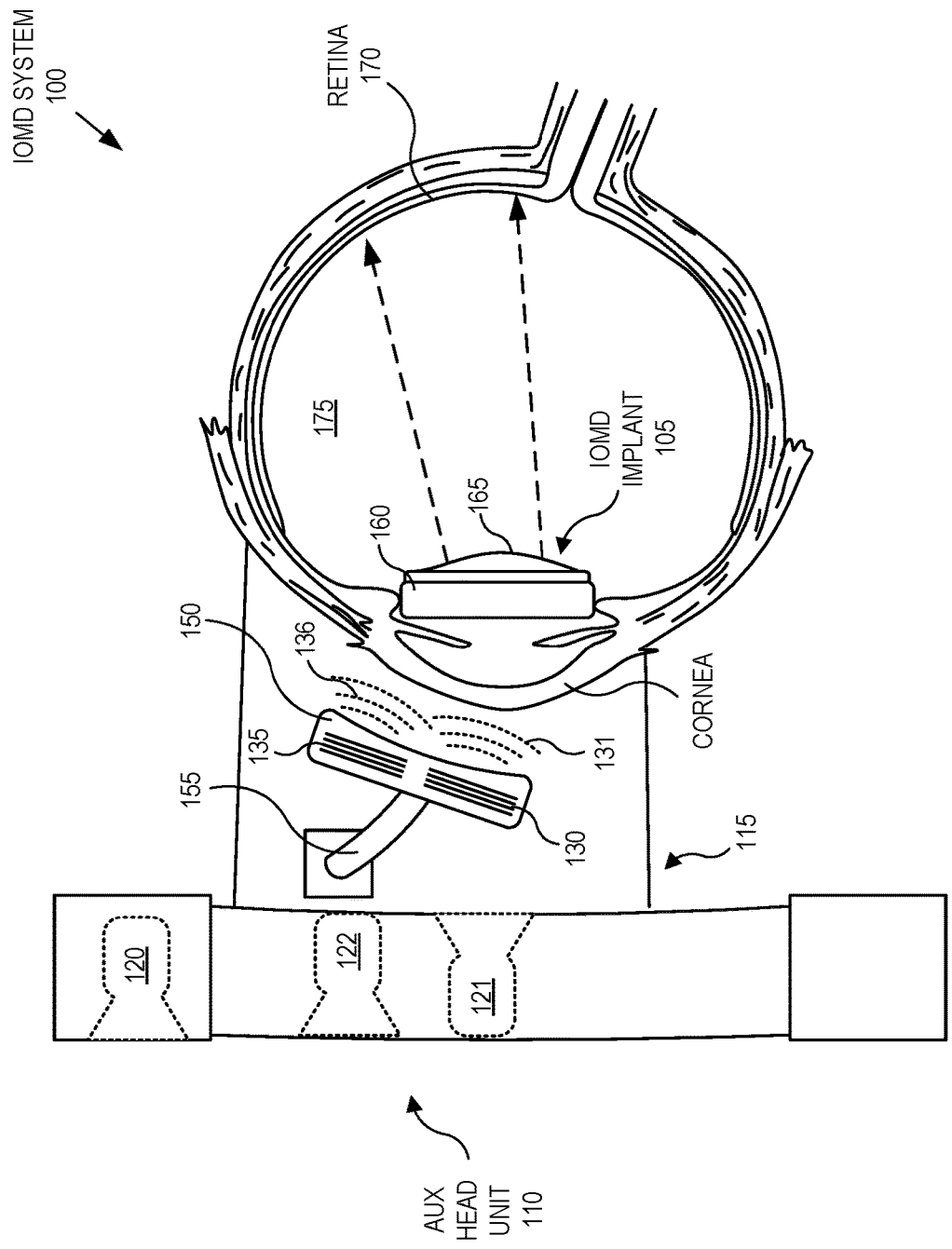
FIG. 1C is a cross-sectional illustration of the IOMD system with the IOMD implant implanted within an eye for projecting regenerated images onto a retina, in accordance with an embodiment of the disclosure.

FIGS. 1A, 1B, and 1C illustrate an IOMD system 100 that includes an IOMD implant 105 and an auxiliary head unit 110, in accordance with an embodiment of the disclosure. FIGS. 1A and 1B are plan and side view illustrations, respectively, while FIG. 1C is a cross-sectional illustration of IOMD system 100. The illustrated embodiment of auxiliary head unit 110 includes a frame 115, a scene camera module 120, a gaze tracking module 121, an autofocus module 122, an antenna mount 125, a charging antenna 130, a data antenna 135, embedded electronic circuitry 140, and a user interface 145. The illustrated embodiment of antenna mount 125 includes a flexible eye-safe enclosure 150 mounted to frame 115 via an articulating arm 155. The illustrated embodiment of IOMD implant 105 includes an enclosure 160 in which electronics are disposed along with focusing optics 165.

During operation auxiliary head unit 110 inductively powers IOMD implant 105 via power signal 131 output from charging antenna 130. Auxiliary head unit 110 further captures forward facing images with scene camera module 120 and wirelessly transmits those images to IOMD implant 105 via data signals 136. In one embodiment, this image capture and transmit is executed in real-time. IOMD implant 105 harvests energy from power signal 131, uses that energy to power receiver and controller circuitry for decoding data signals 136 and display circuitry for projecting a regenerated image onto retina 170 of eye 175. In one embodiment, the regenerated image is only a sub-portion of the scene image captured by scene camera module 120. Again, in one embodiment, the reception, decoding, and display of the image data are executed in real-time and provide the user with virtual, real-time, forward facing vision.

Auxiliary head unit 110 includes frame 115 for mounting auxiliary head unit 110 to the user's head. Although FIGS. 1A-C illustrate frame 115 in the shape of eyeglasses, it should be appreciated that frame 115 may assume a variety of different shapes and configurations for mounting to the user's head including an eyepatch, goggles, visor, headgear, or otherwise. Scene camera module 120 is disposed in or on frame 115 and oriented to acquire scene images in the direction of the user's forward vision. Gaze tracking module 121 is disposed in or on frame 115 in an eye-ward facing orientation to monitor the user's eye 175 and generate gaze direction data. In one embodiment, gaze tracking module 121 is an eye-ward facing camera that generates eye images that may be analyzed to determine the user's gazing direction. In one embodiment, autofocus module 122 is a forward facing infrared (IR) camera that performs conventional autofocus functions.

Antenna mount 125 includes an articulating arm 155 to get at least power antenna 130 close to the user's eye 175 for effective wireless charging of IOMD implant 105. As such, antenna mount 125 includes a flexible eye-safe enclosure 150 in which charging antenna 130 is disposed. In the illustrated embodiment, data antenna 135 is also disposed within flexible eye-safe enclosure 150 for close proximity to IOMD implant 105. In other embodiments, data antenna 135 may be disposed elsewhere within frame 115. In yet another embodiment, power antenna 130 and data antenna 135 may be the same physical antenna operated at different frequencies. Eye-safe enclosure 150 may be fabricated of a variety of soft, flexible, dielectric materials, such as molded silicone, etc.

Although FIGS. 1A-C illustrate auxiliary head unit 115 as a single contiguous frame, in other embodiments, auxiliary head unit 115 may be segmented into two or more body-wearable modular components that may be interconnected and mounted or worn in various locations about the body or clothing. Furthermore, although FIGS. 1A-C illustrate a monocular IOMD system, the illustrated components may be replicated to implement a binocular IOMD system. Furthermore, IOMD implant 105 may be operated with different external hardware having different functionality than described herein in connection with auxiliary head unit 110. In fact, IOMD implant 105 may be operated without a head mounted auxiliary head unit, but rather receive wireless communications from a variety of sources to display a variety of different information.

As illustrated, IOMD implant 105 is entirely disposed within eye 175 and does not include electronic cables or tethers extending out of eye 175 to auxiliary head unit 110. Similarly, auxiliary head unit 110 is an independent, discrete unit that is worn on the user's head. Auxiliary head unit 110 includes embedded electronics for powering and orchestrating the operation of IOMD system 100 including itself and IOMD implant 105.

Figure 1D:
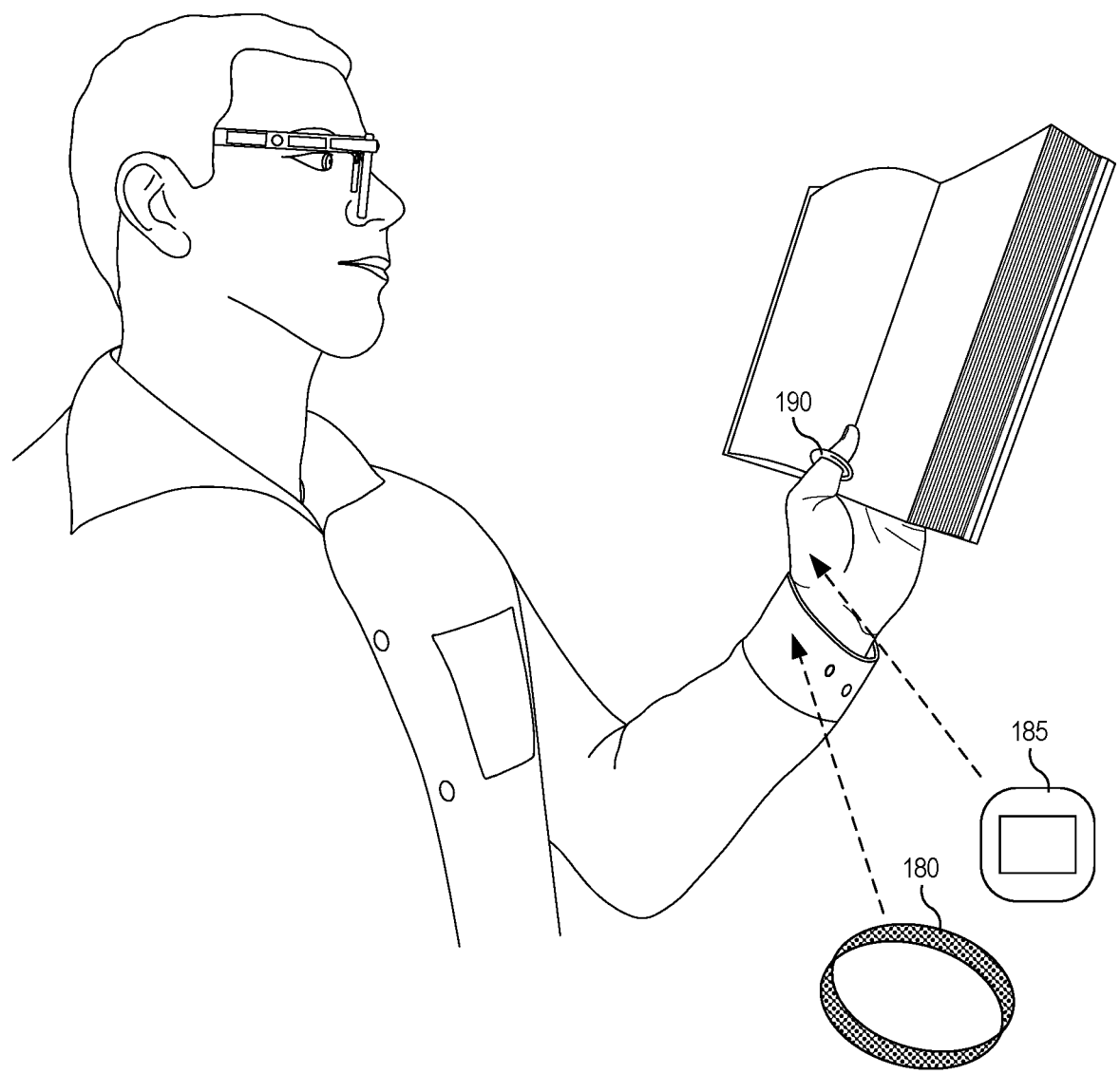
FIG. 1D illustrates use of the IOMD system along with a near-vision fiducial marker to control focal distance of an outward facing scene camera in the auxiliary head unit, in accordance with an embodiment of the disclosure.

FIG. 1D illustrates use of IOMD system 100 along with a near-vision fiducial marker to control the focal distance of scene camera module 120 in auxiliary head unit 110, in accordance with an embodiment of the disclosure. When a user's hands are brought sufficiently into a central region of the user's FOV, it is often the case that the user will want to focus on a task that is using their hands (e.g., reading a book, cooking, tying a shoelace, etc.). Accordingly, in some embodiments, auxiliary head unit 110 is programmed to search for a near-vision fiducial in the FOV of scene camera module 120. The near-vision fiducial may be implemented as an identifiable visual marker. When the identifiable visual marker is found in the FOV of scene camera module 120, the focal distance of scene camera module 120 is automatically adjusted to a near-vision setting that brings the near-vision fiducial marker into focus.

The near-vision fiducial marker may assume a variety of different sizes, shapes, or form factors that are mounted in a variety of different places. For example, the near-vision fiducial marker may be worn on or near a wrist (e.g., bracelet 180), a hand (e.g., sticker or tattoo 185), a finger, a thumb (e.g., ring 190), or otherwise. The identifiable visual marker may be implemented as a visual code (e.g., QR code), an active emitter (e.g., IR emitter), or otherwise. Auxiliary head unit 110 may be programmed to continuously, periodically, or on-demand search for the near-vision fiducial marker. The act of searching for near-vision fiducial marker may include cycling through a plurality of different focal distance settings for scene camera module 120 and searching each scene image acquired at a respective setting for the identifiable visual marker. If the visual marker is identified in one or more of the images, the focal distance setting associated with the scene image having the near-vision fiducial in focus is selected or otherwise locked onto.

Figure 2:
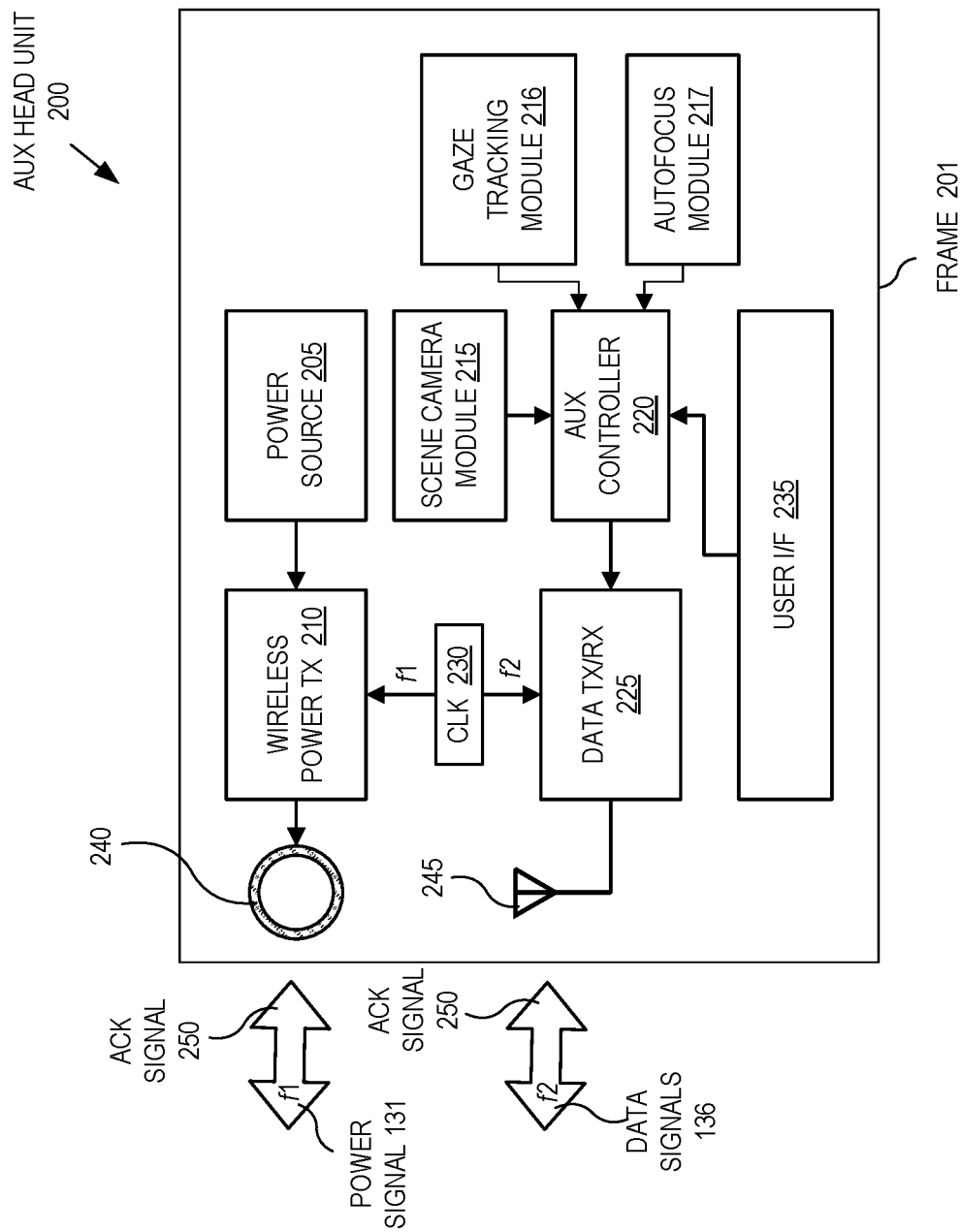
FIG. 2 is a functional block diagram of an auxiliary head unit, in accordance with an embodiment of the disclosure.

FIG. 2 is a functional block diagram of an auxiliary head unit 200, in accordance with an embodiment of the disclosure. Auxiliary head unit 200 is one possible implementation of auxiliary head unit 110. The illustrated embodiment of auxiliary head unit 200 includes a frame 201, a power source 205, a wireless power transmitter 210, a scene camera module 215, a gaze tracking module 216, an autofocus module 217, an auxiliary controller 220, a data transceiver 225, a clock 230, a user interface 235, a power antenna 240, and a data antenna 245.

Power source 205 is provided within frame 201 to power the internal electronics of auxiliary head unit 200 and IOMD implant 105 via inductive power transfer. In one embodiment, power source 205 is a rechargeable battery (e.g., lithium ion battery). IOMD implant 105 is inductively charged via wireless power transmitter 210 and power antenna 240. In one embodiment, wireless power transmitter 210 emits power signal 131 as a continuous wave signal having a sufficiently low frequency f1 (e.g., 13.5 MHz, 27 MHz, etc.) for efficient eye-safe power coupling. The frequency of wireless power transmitter 210 may be based upon clock 230. In one embodiment, clock 230 is a high fidelity, low power resonator, such as a quartz crystal oscillator.

Power source 205 also powers scene camera module 215, gaze tracking module 216, autofocus module 217, auxiliary controller 220, and data transceiver 225. Scene camera module 215 may include a charged coupled device (CCD) sensor, a complementary metal-oxide-semiconductor (CMOS) sensor, or otherwise that acquires the forward-facing scene images, which may then be relayed to IOMD implant 105. In one embodiment, data transceiver 225 transmits the image data representing a sub-portion of the scene image acquired as data signals 136. Data signals 136 are encoded on a carrier signal having a frequency f2 (e.g., 2.4 GHz). Data transceiver 225 may use any number of encoding techniques including one or more of frequency modulation, phase modulation, amplitude modulation, and/or time multiplexing. Frequency f2 can be higher than frequency f1, since it can be transmitted at lower power for safety and provides a higher bandwidth for transmission of still or video images. In some implementations, the relative frequencies of f1 and f2 can be flipped. In one embodiment, frequency f2 is generated based upon clock 230 as well. For example, frequency f2 may be a multiplied or upscaled version of frequency f1, or frequency f1 may be a divided or downscaled version of frequency f2. In either case, clock signals based upon f1 and f2 may be phase aligned to support synchronous data communications where f2 is regenerated at IOMD implant 105 based upon f1.

Auxiliary controller 220 orchestrates the operation of the other functional components. For example, auxiliary controller 220 may receive and decode an acknowledgment (ACK) signal 250 from IOMD implant 105, and in response, adjust the image data sent to IOMD implant 105 to throttle power consumption of IOMD implant 105. ACK signal 250 may be received as a backscatter modulation of power signal 131 on power antenna 240, or received as an actively transmitted signal over data antenna 245. In either case, ACK signal 250 may operate as an acknowledgement that a given image frame has been received and displayed by the IOMD implant 105. Additionally, ACK signal 131 may also include an indication of reception strength of power signal 131 by IOMD implant 105 and/or an indication of operational temperature of IOMD implant 105. Thus, IOMD implant 105 may use a low bandwidth return channel to transmit acknowledgments along with power readings and temperature readings. The acknowledgments, power readings, and temperature readings may then be used by auxiliary controller 220 to throttle power consumption of IOMD implant 105 by adjusting the frame rate and/or color characteristics of the image data transmitted to IOMD implant 105. By regulating the power consumption of IOMD implant 105, auxiliary controller 220 is also regulating the power consumption of auxiliary head unit 200, which is powering IOMD implant 105. Accordingly, the image data may be adjusted due to power scarcity in one or both of IOMD implant 105 or auxiliary head unit 200.

Auxiliary controller 220 may be implemented with hardware logic (e.g., application specific integrated circuit (ASIC), field programmable gate array (FPGA), etc.), implemented with software/firmware instructions stored in memory and executed by a microprocessor, or a combination of both. User interface 235 may include a variety of physical interfaces to enable the user to interact with IOMD system 100. For example, user interface 235 may include a touchpad to receive gesture commands (e.g., swipe forward, swipe back, tap, double tap, etc.), one or more buttons, dials, switches, knobs, a microphone for voice commands, or otherwise. For example, user interface 235 may be enable the user to request on-demand searching for a near-vision fiducial in the FOV of scene camera module 215. In one embodiment, auxiliary controller 220 may generate visual feedback overlays on the acquired images that are transmitted to IOMD implant 105. These visual feedback overlays may include visual acknowledgments when the user interacts with user interface 235, display power readings of power source 205, display operational mode selections, display temperature readings, display a power coupling reading to aid the user in alignment of flexible eye-safe enclosure 150, display acknowledgement of identifying a near-vision fiducial, or otherwise. Of course, IOMD system 100 may include audible feedback to aid alignment of flexible eye-safe enclosure 150 to eye 175.

Gaze tracking module 216 may be implemented using a variety of different technologies for monitoring the user's eye. In one embodiment, gaze tracking module 216 is an eye-ward facing camera that captures eye images for iris or pupil tracking. The position of the iris or pupil in the eye images relative to a reference position may be used to calculate a gazing direction and identify when the user's gaze pans or tilts. In yet another embodiment, a tattoo may be placed on the user's cornea or iris and the position of the tattoo in the eye images used to identify the gazing direction. In yet another embodiment, gaze tracking module 216 may be an electromagnetic sensor (e.g., Hall effect sensor) that monitors an electromagnetic field emitted from IOMD implant 105 or another field emitter implanted in another portion of the eye (e.g., sclera).

Autofocus module 217 provides autofocus functionality to scene camera module 215. In one embodiment, autofocus module 217 includes an IR emitter and sensor. Other known active, passive, or hybrid variants for providing autofocus functionality, either independent of, or integrated with, scene camera module 215 may be implemented.

Figure 3:
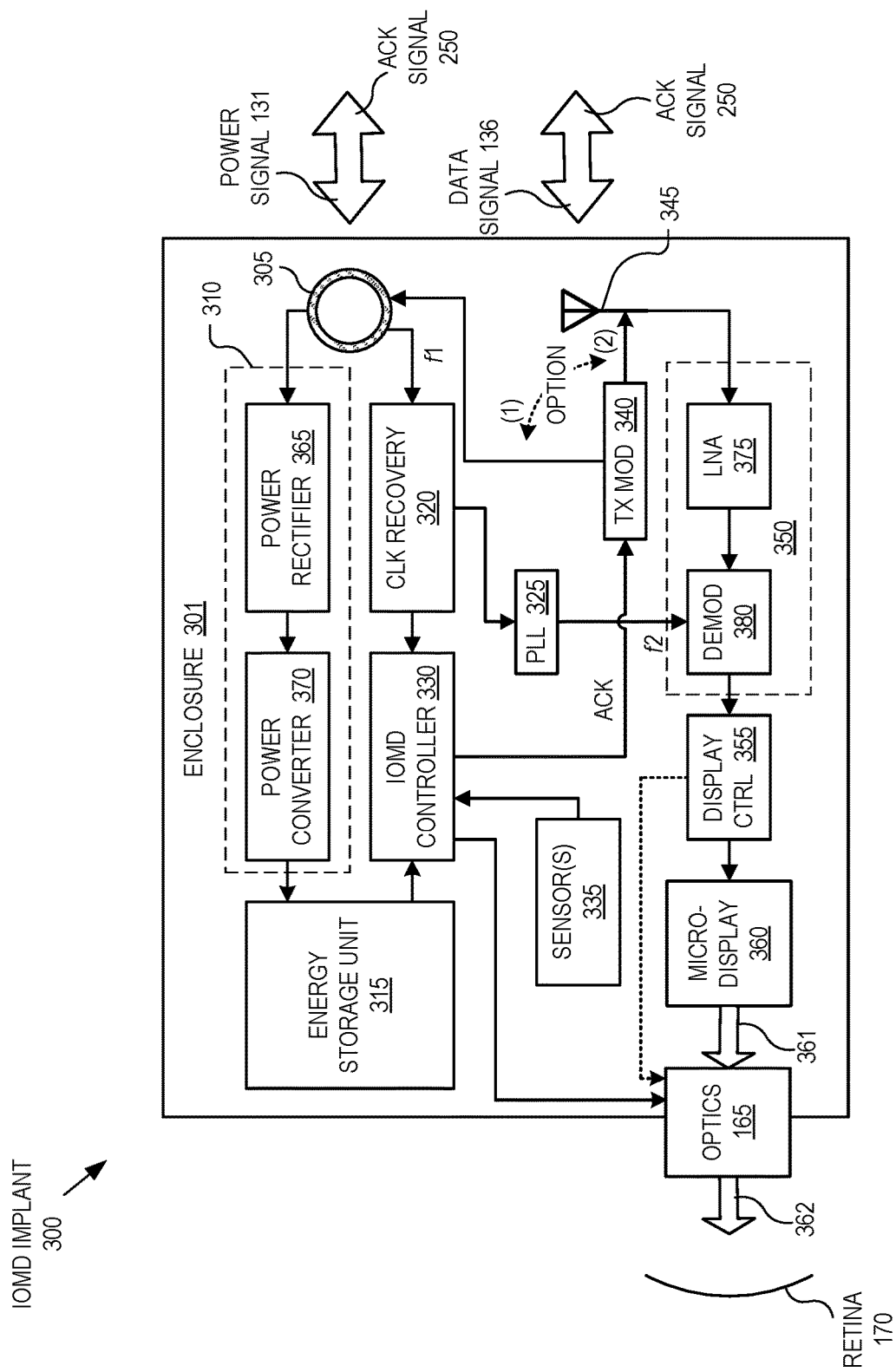
FIG. 3 is a functional block diagram of an IOMD implant, in accordance with an embodiment of the disclosure.

FIG. 3 is a functional block diagram of an IOMD implant 300, in accordance with an embodiment of the disclosure. IOMD implant 300 represents one possible implementation of IOMD implant 105. The illustrated embodiment of IOMD implant 300 includes an enclosure 301, a power antenna 305, power harvesting circuitry 310, an energy storage unit 315, clock recovery circuitry 320, a phase lock loop (PLL) 325, an IOMD controller 330, one or more sensors 335, a transmit module 340, a data antenna 345, receiver circuitry 350, a display controller 355, a micro-display 360, and optics 165. The illustrated embodiment of power harvesting circuitry 310 includes a power rectifier 365 and a power converter 370. The illustrated embodiment of receiver circuitry 350 includes a low noise amplifier (LNA) 375 and a demodulator 380.

In the illustrated embodiment, the electronic components of IOMD implant 300 are housed within a biocompatible enclosure 301 that is sized and shaped for implantation into eye 175. In one embodiment, enclosure 301 is sized for implantation into the region of the capsular sack of eye 175. In one embodiment, enclosure 301 is a hermetically sealed enclosure fabricated of metal, polymers, or otherwise.

During operation, power signal 131 output from auxiliary head unit 110 is incident upon power antenna 305. In various embodiments, power antenna 305 is disposed in or on enclosure 301. In yet other embodiments, power antenna 305 may be externally attached or tethered to enclosure 301, and implanted into another region of eye 175, such as under the sclera. In one embodiment, power antenna 305 is a loop antenna suitable for harvesting inductive power operating at frequency f1. Power harvesting circuitry 310 is coupled to power antenna 305 to harvest the wireless power incident thereon. Power harvesting circuitry 310 includes power rectifier 365 and power converter 370. In one embodiment, power rectifier 365 is implemented with one or more diodes for rectification while power converter 370 is implemented as a direct current (DC) to DC buck converter. Other power harvesting circuitry components may be used. Power harvesting circuitry 310 is used to charge energy storage unit 315. In one embodiment, energy storage unit 315 is implemented with a capacitor, such as a supercapacitor. In yet other embodiments, a rechargeable battery may be implemented, though such implementations may have a shorter life span, and thus requiring periodic surgical replacement. Alternatively, energy storage unit 315 may be implanted into another region of eye 175 (e.g., under the sclera) and tethered to enclosure 301. Placing a battery within the sclera may provide for less invasive replacement procedures. However, the components may all be implanted into eye 175, and thus less susceptible to infection compared to a transcutaneous tether extending external to the eye.

Clock recovery circuitry 320 is also coupled to power antenna 305 to extract and recover a synchronous clock signal from power signal 131 from auxiliary head unit 200. Accordingly, clock recovery circuitry 320 operates to recover the lower frequency ft from the carrier wave of power signal 131. Frequency ft (or a partial/whole multiple thereof) is then provided to the other circuit components of IOMD implant 300 for synchronous timing. In particular, PLL 325 may be used to lock onto the phase of the synchronous clock output from clock recovery 320 and an upconverted frequency f2 provided to receiver circuitry 350 to synchronously demodulate data signal 136 received from auxiliary head unit 200 over data antenna 345. Receiver circuitry 350 includes LNA 375 to amplify data signal 136 and demodulator 380 to down convert and decode the higher frequency f2 data signal 136. Demodulator 380 may be implemented using a variety of decoding circuits, such as, an energy detect circuit, an IQ receiver, or otherwise. Data signals 136 may be modulated using one or more of frequency modulation, phase modulation, amplitude modulation, quadrature modulation, etc.

The decoded data signals 136 are then provided to display controller 355 as the image data to be displayed by micro-display 360. Display controller 355 may be a discrete controller from IOMD controller 330 (e.g., integrated into micro-display 360) or may be logic functions/instructions executed on IOMD controller 330 for the purpose of controlling operation of micro-display 360. In one embodiment, micro-display 360 is implemented as a multi-color light emitting diode (LED) display array. In other embodiments, micro-display 360 is a backlit liquid crystal display (LCD), a monochrome LED display array, an organic LED (OLED) display, or otherwise. In one embodiment, micro-display 360 has 5 mm diameter display while enclosure 301 has an overall 10 mm×10 mm size. Micro-display 360 outputs the image based upon the received image data, which is projected through focusing optics 165 onto retina 170.

IOMD implant 300 also includes IOMD controller 330, which serves to orchestrate the operation of the other functional components of IOMD implant 300. As with auxiliary controller 220, IOMD controller 330 may be implemented in hardware logic, implemented in software/firmware logic stored to a machine readable medium and executed by a microcontroller, or implemented in a combination of both.

In the illustrated embodiment, IOMD controller 330 is coupled to receive sensor readings from one or more sensors 335. Sensor(s) 335 may include a temperature sensor to monitor the operational temperature of IOMD implant 300. In this regard, the temperature sensor is a proxy reading for power consumption or power dissipation within IOMD implant 300. The temperature sensor also serves as a safety measure to ensure the eye tissue surrounding IOMD implant 300 is not damaged due to elevated operational temperatures.

In one embodiment, sensors 335 also include a voltage sensor coupled to energy storage unit 315 to measure and monitor the voltage across the electrodes of energy storage unit 315, and thus measure the stored energy. The measured voltage across energy storage unit 315 may also serve as a proxy for, or an indication of, the reception strength of power signal 131. Alternatively, sensors 335 may be coupled to power harvesting circuitry 310 and/or power antenna 305 to directly measure received voltage.

In one embodiment, sensors 335 include an eyelid sensor for determining the open or closed state of the user's eyelid and even monitoring for eyelid blinks. The eyelid sensor may be implemented using an outward facing photosensor (e.g., photodiode) that monitors for changes in incident light intensity. In one embodiment, the photosensor may monitor for interruptions of an IR beam emitted from auxiliary head unit 110 and through the pupil onto IOMD implant 105. Alternatively, the eyelid sensor may be implemented by monitoring the signal strength of power signal 131 and/or data signal 136 received from auxiliary head unit 110. The intervening position of the eyelid may modulate these signals in an identifiable manner that may be correlated to eyelid position. In yet another embodiment, the eyelid sensor may be implemented using an impedance sensor that emits an electromagnetic field that is influenced by the open or closed state of the eyelid. Whatever the implementation, the eyelid sensor may be used to generate an indication of when the eyelid is closed, which indication may then be used to temporarily disable micro-display 360, or otherwise cease projecting regenerated image 361 to simulate the temporary loss of light or vision when closing or blinking one's eyes.

Alternatively (or additionally), sensing eyelid closure may be executed at auxiliary head unit 200 using gaze tracking module 216 or another eye-ward facing camera and determined by auxiliary controller 220. In this embodiment, data signals 136 may be encoded with the eye closure indication, or data signals 136 may simply cease transmitting, or temporarily transmit a black image instead of the scene image or sub-portion thereof.

IOMD controller 330 further includes logic for generating the ACK signal, which is transmitted back to the auxiliary head unit 200 via transmit module 340 as a feedback data path. Auxiliary head unit 200 uses the ACK signal to manage overall system power consumption by adjusting frame rates, color fading, and transmit power. The ACK signal may operate as an acknowledgment of each received image frame, an indication that the data frame was correctly received and displayed, an indication of the operating temperature of IOMD implant 300, and an indication of reception strength (or a proxy thereof, such as voltage level on energy storage unit 315).

FIG. 3 illustrates two options for implementing the feedback data path. Option (1) illustrates transmit module 340 coupled to power antenna 305 to provide the feedback data path over the lower frequency f1 wireless power charging path. With option (1), transmit module 340 operates as an RFID tag to modulate the impedance of power antenna 305 and generate ACK signal 250 as a backscatter modulation of power signal 131. Option (2) illustrates transmit module 340 coupled to data antenna 345 to provide the feedback data path over the high frequency f2 wireless data signal path. With option (2), transmit module 340 is an active transmitter for generating ACK signal 250. Of course, options (1) and (2) need not be mutually exclusive, but rather, in some embodiments, both options may be implemented and used selectively based upon available power budget and bandwidth needs for the feedback data path.

In one embodiment, power antenna 305 is shaped as a loop antenna to harvest radio frequency or microwave frequency wireless power. However, it should be appreciated that power antenna 305 may assume a variety of sizes and shapes to harvest power from various frequencies of electromagnetic (EM) radiation. Similarly, data antenna 345 may assume a variety of different sizes and shapes to effectively receive (and optionally transmit) data signals 136 and/or ACK signal 250 at the higher frequency f2 (e.g., 2.4 GHz or otherwise). For example, data antenna 345 may be a dipole antenna, a patch antenna, or otherwise. In one embodiment, data antenna 345 is an optical antenna (e.g., photo receiver or photo transceiver) and data signals 136 are optical wavelength EM radiation. In yet another embodiment, power antenna 305 and data antenna 345 may be implemented as a single physical antenna that is shared between power harvesting circuitry 310, receiver circuitry 350, and transmit module 340. In this shared embodiment, power antenna 305 and data antenna 345 are graphical representations of the different functional uses for a single physical antenna.

Finally, FIG. 3 illustrates optics 165, which provide the optical power for focusing the regenerated image 361 output from micro-display 360 onto retina 170. Optics 165 may include a high-power base lens (e.g., 100 diopters or more) along with one or more adjustable components. These adjustable components may include an adjustable power lens that provides an adjustable focal distance (z-axis adjustment) to regenerated image 361. In various embodiments, optics 165 further include one or more adjustable prisms that provide beam steering for lateral adjustments (x and/or y axis adjustment) of the position of the projected image 362. Lateral adjustments ensure that projected image 362 is properly positioned/centered on retina 170 including the user's fovea. Regenerated image 361 and/or projected image 362 may be referred to herein as the image, the regenerated image, or the projected image, but all refer to the image output from micro-display 360 whether or not it has been lensed or beam steered by optics 165.

Figure 4:
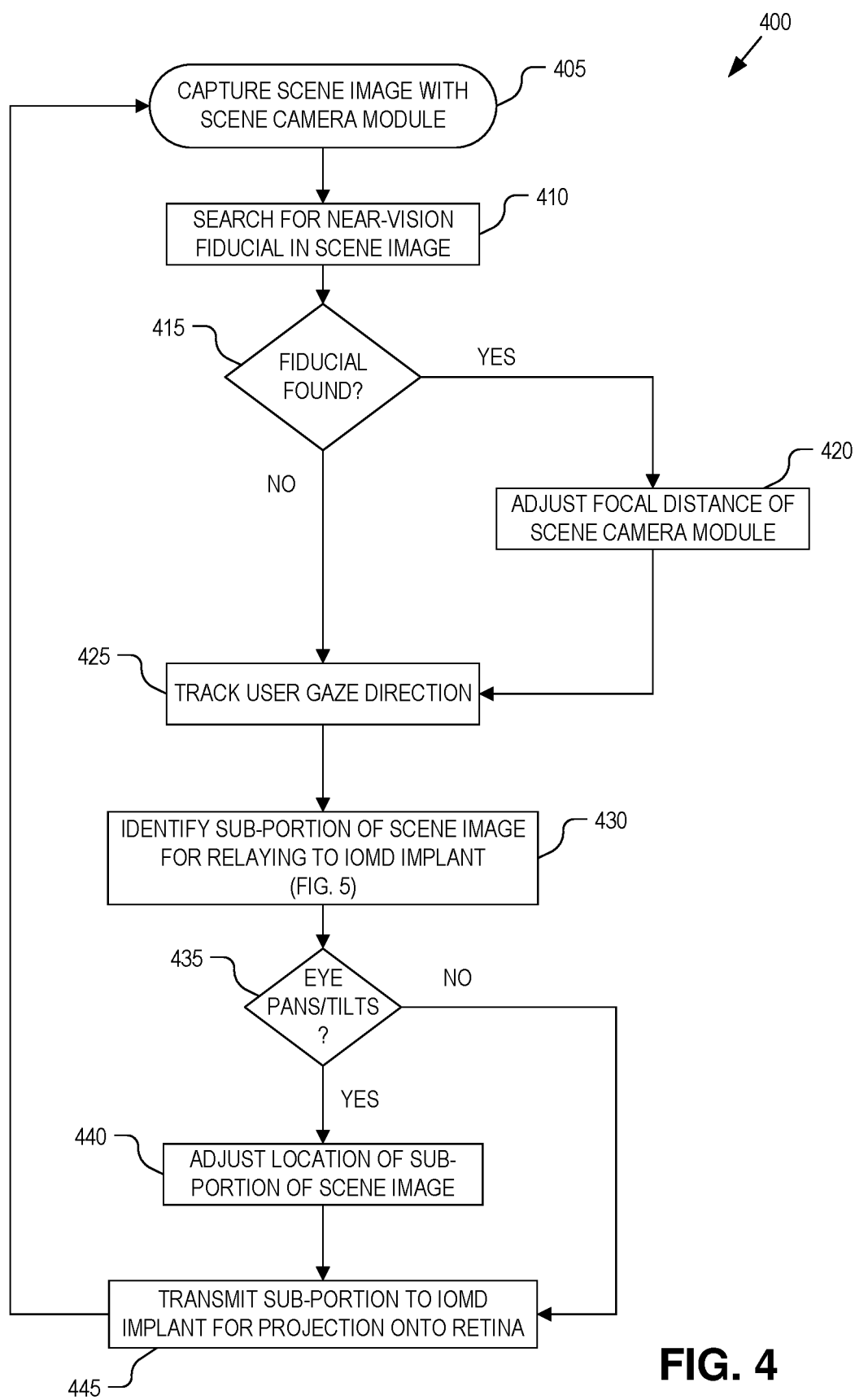
FIG. 4 is a flow chart illustrating a process of operation of the IOMD system to provide pan/tilt and autofocus control over the IOMD system, in accordance with an embodiment of the disclosure.

FIG. 4 is a flow chart illustrating a process 400 of operation of IOMD system 100 to provide pan/tilt and autofocus control over IOMD system 100, in accordance with an embodiment of the disclosure. Process 400 is described with reference to the system illustrated in FIGS. 1A-D. However, process 400 is also applicable to the embodiments illustrated in FIGS. 3 and 4, and in certain instances, components illustrated in those figures are referenced. The order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

In a process block 405, a scene image of a user's forward facing FOV is captured with scene camera module 120. In one embodiment, the scene image is a high-resolution image captured in real-time (or near real-time) as it is wirelessly conveyed to IOMD implant 105 and projected to the user's retina 170.

Upon capturing a scene image, auxiliary controller 220 analyzes/searches the scene image for a near-vision fiducial (process block 410). Auxiliary controller 220 may continuously analyze all captured scene images, periodically analyze only select scene images (e.g., every Nth image frame), or analyze captured scene images on demand. On-demand searching may commence in response to the user requesting IOMD system 100 enter a near-vision mode of operation. Such a command may be received via user interface 145 (or 235). As mentioned above, auxiliary head unit 110 may cycle scene camera module 215 through a plurality of different focal distance settings while it searches for an instance of the near-vision fiducial.

If a near-vision fiducial is not identified (decision block 415), then process 400 continues to a process block 425 to perform gaze tracking. However, if a near-vision fiducial is identified (decision block 415), then process 400 continues to a process block 420. In process block 420, the focal distance setting of scene camera module 120 is adjusted to bring the identified near-vision fiducial into focus. In other words, the focal distance setting that brings the near-vision fiducial into focus is identified and automatically held, and/or continuously updated, to maintain acceptable or optimal focus. The near-vision fiducial provides a focusing target for scene camera module 120.

In a process block 425, gaze tracking is executed with the aid of gaze tracking module 121. Gaze tracking module 121 is oriented to monitor the user's eye 175 and generate real-time gaze direction data. In one embodiment, the gaze direction data includes eye images acquired by an eye-ward facing camera implementation of gaze tracking module 121. The eye images may be analyzed by auxiliary controller 220 to determine a gazing direction. The gaze direction may be determined based upon a position of the pupil or iris in the eye images relative to a reference position. Alternatively, a tattoo may be formed on the user's cornea and operate as an eye fiducial. The position of the eye fiducial may then be tracked relative to a reference position. The reference position may be factory set or user calibrated by performing a calibration or setup routine. Of course, other gaze tracking schemes may be implemented. For example, a Hall effect sensor may be used to track the position of a magnetic eye fiducial implanted into the sclera or other portions of the eye. In yet another embodiment, IOMD implant 105 itself may operate as the eye fiducial. In this embodiment, the IOMD implant 105 may be a passive fiducial or active fiducial that emits a trackable signal.

In one embodiment, the gazing direction is determined with reference to a single eye. In another embodiment, auxiliary head unit 110 may include a binocular gaze tracking module that monitors both eyes (e.g., two separate eye-ward facing camera modules). With a binocular gaze tracking module, gaze tracking not only determines the direction of a user's gaze but also identifies whether the user is using their near-vision based upon whether both eyes turn inward, as opposed to both tracking the same direction for distance vision. In one embodiment, an identification of the user attempting to use their near-vision may be an on-demand trigger to search for a near-vision fiducial in a scene image (process block 410).

Figure 5:
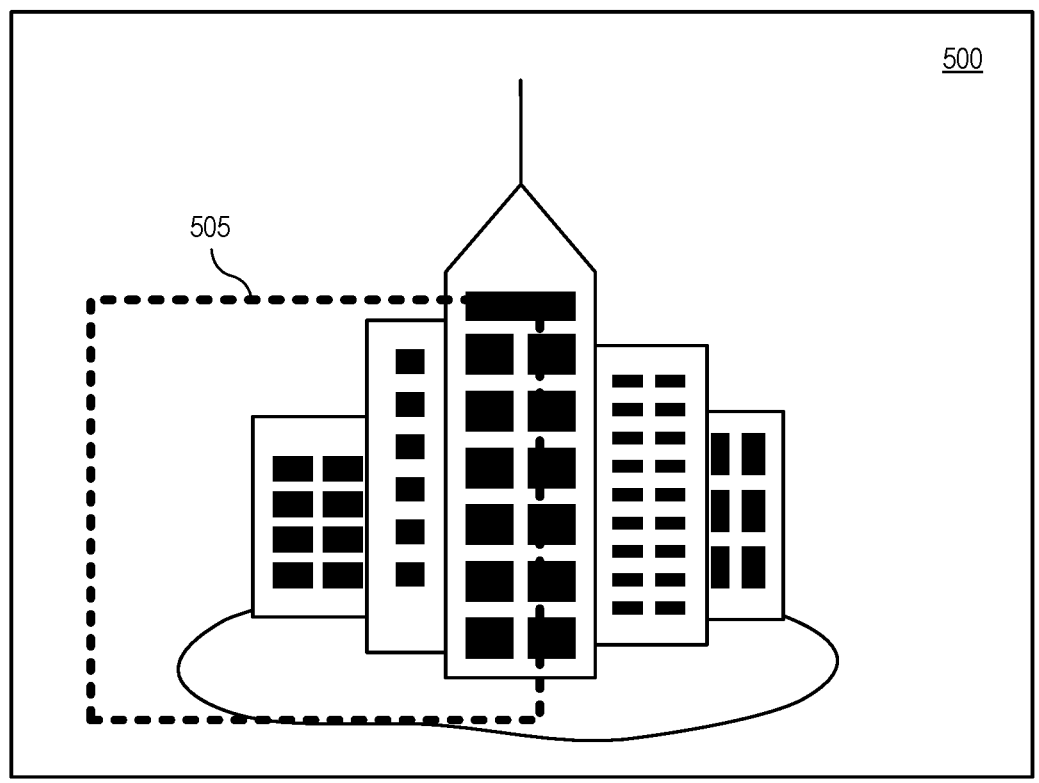
FIG. 5 illustrates how a sub-portion of the higher resolution scene image is selected and transmitted from the auxiliary head unit to the IOMD implant for projection onto a retina, in accordance with an embodiment of the disclosure.

Once a gazing direction has been determined, auxiliary controller 220 can use this information to identify a sub-portion of the high-resolution scene image for relaying to IOMD implant 105 (process block 430). FIG. 5 illustrates an example of identifying a sub-portion 505 of a scene image 500. In this example, auxiliary controller 220 has determined based upon the gaze direction data (e.g., one or more eye images) that the user is looking down and to the left. Accordingly, auxiliary controller 220 selects sub-portion 505 correlated to this gazing direction for wireless relay to IOMD implant 105 via data antenna 135. The size of sub-portion 505 may be selected based upon the bandwidth/power constraints of the wireless data channel between auxiliary head unit 110 and IOMD implant 105 and/or the image resolution capabilities of micro-display 360 within IOMD implant 105. By identifying and selecting sub-portion 505 of scene image 500 based upon the user's eye movement and gazing direction, the user's natural physio-optical response to pan and tilt eye movements is simulated, thereby providing a natural user experience. When the user's pans or tilts their eyes (decision block 435), sub-portion 505 is moved about the larger scene image 500 simulating natural eye movement. In other words, auxiliary head unit 110 adjusts and continuously readjusts the location of sub-portion 505 within scene image 500 in real-time. As changes in the user's gazing direction are determined, the position of sub-portion 505 within scene image 500 is revised (process block 440), thus updating the image data (i.e., revised sub-portion) that is relayed to IOMD implant 105 for projection onto retina 170 (process block 445).

Figure 6:
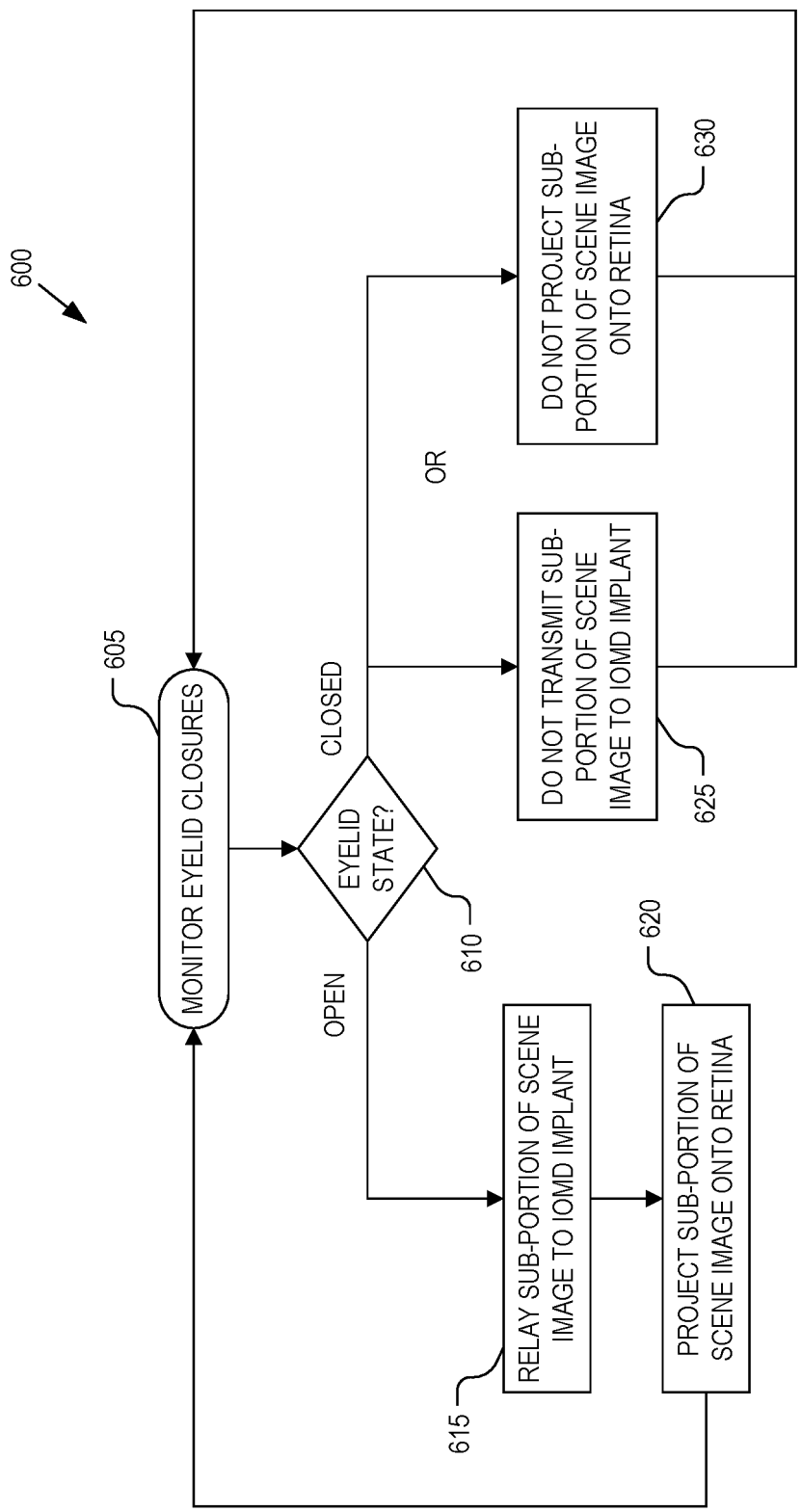
FIG. 6 is a flow chart illustrating blink control over the IOMD system, in accordance with an embodiment of the disclosure.

FIG. 6 is a flow chart illustrating a process 600 for blink control over IOMD system 100, in accordance with an embodiment of the disclosure. Process 600 is described with reference to the system illustrated in FIGS. 1A-D. However, process 600 is also applicable to the embodiments illustrated in FIGS. 3 and 4, and in certain instances, components illustrated in those figures are referenced. The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel.

In a process block 605, IOMD system 100 monitors the closure state of the user's eyelid. In one embodiment, the closure state of an eyelid may be monitored by auxiliary head unit 110 using gaze tracking module 121. For example, an eye-ward facing camera may visually monitor an eyelid for eyelid closures or blinks. In one embodiment, the closure state of the eyelid may be monitored by IOMD implant 105 from the inside out. Eyelid monitoring by IOMD implant 105 may be implemented using an outward looking photo-sensor (e.g., photodiode) that tracks changes in light intensity or monitors interruptions of an IR beam broadcast from auxiliary head unit 110. Alternatively, IOMD implant 105 may sense fluctuations in the signal strength of data signals 136 and/or the coupling strength of power signals 131 from auxiliary head unit 110 (or 200). Fluctuations in these signals may correlate to whether the eyelid is open or closed. In yet another embodiment, IOMD implant 105 may include an impedance sensor capable of monitoring fluctuations in an oscillation circuit that inductively couples to the eyelid of the user. Of course, one or more of the above techniques, or other eyelid sensing techniques, may be implemented.

In a decision block 610, if the eyelid is determined to be open, then auxiliary head unit 110 wirelessly relays data signals 136, including sub-portion 505 of scene image 500, to IOMD implant 105 (process block 615). In turn, IOMD implant 105 projects a regenerated image of sub-portion 505 onto the user's retina 170 (process block 620). On the other hand, if the user's eyelid is determined to be closed (decision block 610), then the regenerated image is temporarily interrupted while the eyelid is deemed closed. The regenerated image may be temporarily interrupted at the behest of auxiliary head unit 110 or IOMD implant 105. In process block 625, if auxiliary head unit 110 determines that the eyelid is closed, then auxiliary head unit 110 can either not transmit sub-portion 505, transmit an indication that the eyelid is currently deemed closed, and/or transmit a black image in place of sub-portion 505 of scene image 500. Correspondingly, if IOMD implant 105 determines that the eyelid is closed (e.g., using one of the on-board sensors 335), then IOMD implant 105 (or 300) may independently disable micro-display 360 while the closed state is deemed to persist (process block 630). Of course, in some embodiments, both auxiliary head unit and IOMD implant mechanisms for determining eyelid closures and temporarily ceasing projection of the regenerated image may be implemented together.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An intraocular micro-display (IOMD) system, comprising:
    a head mounted device including:
    a camera that is forward facing of a user;
    a controller configured to:
    acquire one or more images with the camera, wherein each image of the one or more images is acquired at a corresponding focal distance;
    search the one or more images for a near-vision fiducial that includes an identifiable visual marker that is worn on or near the user;
    identify a first image of the one or more images as bringing the near-vision fiducial into focus;
    adjust a focal distance of the camera to an adjusted focal distance, wherein the adjusted focal distance is associated with the first image;
    acquire a second image with the camera having the adjusted focal distance; and
    wirelessly relay image data based on the second image to an IOMD implant for display to a retina of an eye of the user.

2. The IOMD system of claim 1 further comprising a sensor for generating gaze direction data of the eye of the user,
    wherein the controller is further configured to:
        determine a gazing direction of the eye based on the gaze direction data; and
        identify a sub-portion of the second image based on the gazing direction,
    wherein the image data comprises the sub-portion of the second image.

3. The IOMD system of claim 2, wherein the sub-portion is a first sub-portion,
    wherein the controller is further configured to:
    determine a revised gazing direction of the eye based on the gaze direction data;
    identify a second sub-portion of the second image based on the revised gazing direction; and
    wirelessly relay the second sub-portion to the IOMD implant for display.

4. The IOMD system of claim 3,
    wherein the revised gazing direction of the eye is in response to a panning or a tilting of the eye,
    wherein the IOMD implant displays the second sub-portion as movement of the first sub-portion at a first location in the second image to a second location in the second image according to the panning or the tilting of the eye.

5. The IOMD system of claim 1 further comprising the IOMD implant shaped for implantation into the eye, the IOMD implant including a micro-display for projecting a regenerated image of the second image onto the retina when the IOMD implant is implanted into the eye.

6. The IOMD system of claim 1, wherein the identifiable visual marker is worn on or near a wrist, a hand, a finger, or a thumb of the user.

7. The IOMD system of claim 1, wherein the controller is configured to search the first image in response to receiving user input via a user interface of the head mounted device.

8. A head mounted device for communicating with an intraocular micro-display (IOMD) implant, the head mounted device comprising:
    a forward-facing camera; and
    a controller configured to:
    acquire one or more images with the camera, wherein each image of the one or more images is acquired at a corresponding focal distance;
    search the one or more images for a near-vision fiducial that comprises an identifiable visual marker that is worn on or near a user of the head mounted device;
    identify a first image of the one or more images as bringing the near-vision fiducial into focus;
    adjust a focal distance of the forward-facing camera to an adjusted focal distance, wherein the adjusted focal distance is associated with the first image;
    acquire a second image with the forward-facing camera having the adjusted focal distance; and
    relay image data based on the second image to the IOMD implant for display to a retina of an eye of the user.

9. The head mounted device of claim 8 further comprising an eye-ward facing camera for generating gaze direction data of the eye of the user,
wherein the controller is further configured to:
determine a gazing direction of the eye based on the gaze direction data; and
identify a sub-portion of the second image based on the gazing direction,
wherein the image data comprises the sub-portion of the second image.

10. The head mounted device of claim 9, wherein the sub-portion is a first sub-portion,
wherein the controller is further configured to:
determine a revised gazing direction of the eye based on the gaze direction data;
identify a second sub-portion of the second image based on the revised gazing direction; and
wirelessly relay the second sub-portion to the IOMD implant for display.

11. The head mounted device of claim 9, wherein the gaze direction data comprises an eye image of the eye captured by the eye-ward facing camera, wherein the controller determines the gazing direction by:
identifying an eye fiducial in the eye image, wherein the eye fiducial is disposed in or on the eye; and
determining a position of the eye fiducial within the eye image relative to a reference position.

12. The head mounted device of claim 11, wherein the eye fiducial comprises a tattoo disposed on a cornea or an iris of the eye.

13. The head mounted device of claim 8 further comprises a user interface, wherein the controller is configured to search the first image in response to receiving user input via the user interface.

14. A method performed by at least one processor of an intraocular micro-display (IOMD) system that comprises a head mounted device and an IOMD implant, the method comprising:
receiving one or more images captured by a camera of the head mounted device that is forward facing of a user of the head mounted device, wherein each image of the one or more images is acquired at a corresponding focal distance;
searching the one or more images for a near-vision fiducial that includes an identifiable visual marker that is worn on or near the user;
adjusting a focal distance of the camera to an adjusted focal distance, wherein the adjusted focal distance is associated with one of the one or more images;
receiving a second image captured by the camera having the adjusted focal distance; and
transmitting image data based on the second image to the IOMD implant for display to a retina of an eye of the user when the IOMD implant is implanted into the eye of the user.

15. The method of claim 14 further comprising:
determining a gazing direction of the eye based on gaze direction data of the eye of the user generated by a sensor of the head mounted device; and
identifying a sub-portion of the second image based on the gazing direction,
wherein the image data comprises the sub-portion of the second image.

16. The method of claim 15 further comprising:
determining a revised gazing direction of the eye based on the gaze direction data;
identifying a revised sub-portion of the second image based on the revised gazing direction; and
transmitting the revised sub-portion to the IOMD implant for display.

17. The method of claim 15, wherein the sensor comprises an eye-ward facing camera and the gaze direction data comprises an eye image of the eye captured by the eye-ward facing camera, wherein determining the gazing direction comprises:
identifying an eye fiducial in the eye image, wherein the eye fiducial is disposed in or on the eye; and
determining a position of the eye fiducial within the eye image relative to a reference position.

18. The method of claim 17, wherein the eye fiducial comprises a tattoo disposed on a cornea or an iris of the eye.

19. The method of claim 14, wherein the identifiable visual marker is worn on or near a wrist, a hand, a finger, or a thumb of the user.

* * * * *